US009333112B2

(12) United States Patent  
Carson

(10) Patent No.: US 9,333,112 B2
(45) Date of Patent: May 10, 2016

(54) SORPTION-BASED ADHESIVE CONTACT COOLING APPARATUS AND METHOD

(75) Inventor: Gary A. Carson, Golden, CO (US)

(73) Assignee: Medivance Incorporated, Louisville, CO (US)

( * ) Notice: Subject to any disclaimer, the term of this patent is extended or adjusted under 35 U.S.C. 154(b) by 2435 days.

(21) Appl. No.: 12/101,610

(22) Filed: Apr. 11, 2008

(65) Prior Publication Data

US 2008/0255644 A1 Oct. 16, 2008

Related U.S. Application Data

(60) Provisional application No. 60/911,464, filed on Apr. 12, 2007.

(51) Int. Cl.
A61F 7/10 (2006.01)
A61F 7/00 (2006.01)
A61F 7/02 (2006.01)

(52) U.S. Cl.
CPC . *A61F 7/10* (2013.01); *A61F 7/106* (2013.01); A61F 2007/0068 (2013.01); A61F 2007/0226 (2013.01); A61F 2007/0246 (2013.01)

(58) Field of Classification Search
CPC .................................. A61F 7/106; A61F 7/10
USPC .................................................... 607/104, 96
See application file for complete search history.

(56) References Cited

U.S. PATENT DOCUMENTS

| 2,250,325 A | 7/1941 | Barnes |
| 2,726,658 A | 12/1955 | Chessey |
| 3,091,242 A | 5/1963 | Johnson, Jr. et al. |
| 3,212,286 A | 10/1965 | Curtis |
| 3,734,293 A | 5/1973 | Biskis |
| 3,867,939 A | 2/1975 | Moore et al. |
| 3,927,671 A | 12/1975 | Chittenden et al. |
| 3,995,621 A | 12/1976 | Fletcher et al. |
| 4,108,146 A | 8/1978 | Golden |
| 4,114,620 A | 9/1978 | Moore et al. |
| 4,118,946 A | 10/1978 | Tubin |
| 4,149,541 A | 4/1979 | Gammons et al. |
| 4,154,245 A | 5/1979 | Daily |

(Continued)

FOREIGN PATENT DOCUMENTS

WO PCT/IL99/00059 A1 9/1999
WO PCT/US03/010311 A2 10/2003

*Primary Examiner* — Nathan R Price
*Assistant Examiner* — Melissa A Snyder
(74) *Attorney, Agent, or Firm* — Marsh Fischmann & Breyfogle LLP

(57) ABSTRACT

A sorption-based, adhesive contact apparatus and method for contact cooling a patient via conductive thermal exchange are described. The apparatus includes a pad, having a fluid containing layer and adhesive contact surface, and a sorption-based device, fluidly interconnectable to the fluid containing layer, for vaporizing fluid contained in the fluid containing layer and for sorping the vaporized fluid. The fluid vaporization and the vapor sorption cools the adhesive contact surface of the pad. A port control member may selectively establish fluid interconnection between the fluid containing layer and sorption-based device. An internal pressure of the sorption-based device may be established lower than an internal pressure of the fluid-containing layer prior to fluid interconnection therebetween. A fluid retention member and path defining members may be included to facilitate vaporization, vapor diffusion and vapor sorption, thereby enhancing uniform cooling.

24 Claims, 3 Drawing Sheets

(56) References Cited

U.S. PATENT DOCUMENTS

| | | | |
|---|---|---|---|
| 4,161,210 A | 7/1979 | Reid et al. | |
| 4,195,631 A | 4/1980 | Baucom | |
| 4,444,727 A | 4/1984 | Yanagihara et al. | |
| 4,508,123 A | 4/1985 | Wyatt et al. | |
| 4,580,408 A | 4/1986 | Stuebner | |
| 4,834,705 A | 5/1989 | Vaillancourt | |
| 4,919,134 A | 4/1990 | Streeter | |
| 4,962,761 A | 10/1990 | Golden | |
| 5,000,252 A | 3/1991 | Faghri | |
| 5,062,414 A | 11/1991 | Grim | |
| 5,097,829 A | 3/1992 | Quisenberry | |
| 5,111,668 A | 5/1992 | Parrish et al. | |
| 5,113,666 A | 5/1992 | Parrish et al. | |
| 5,133,348 A | 7/1992 | Mayn | |
| 5,190,032 A | 3/1993 | Zacoi | |
| 5,268,022 A | 12/1993 | Garrett et al. | |
| 5,289,695 A | 3/1994 | Parrish et al. | |
| 5,304,213 A | 4/1994 | Berke et al. | |
| 5,383,919 A | 1/1995 | Kelly et al. | |
| 5,411,541 A | 5/1995 | Bell et al. | |
| 5,423,751 A | 6/1995 | Harrison et al. | |
| 5,466,250 A | 11/1995 | Johnson, Jr. et al. | |
| 5,470,353 A | 11/1995 | Jensen | |
| 5,486,207 A | 1/1996 | Mahawili | |
| 5,514,169 A | 5/1996 | Dickerhoff et al. | |
| 5,545,194 A | 8/1996 | Augustine | |
| 5,609,620 A | 3/1997 | Daily | |
| 5,624,477 A | 4/1997 | Armond | |
| 5,658,325 A | 8/1997 | Augustine | |
| 5,662,695 A | 9/1997 | Mason et al. | |
| 5,683,439 A | 11/1997 | Jensen | |
| 5,733,318 A | 3/1998 | Augustine | |
| 5,806,335 A | 9/1998 | Herbert et al. | |
| 5,887,437 A | 3/1999 | Maxim | |
| 5,913,849 A | 6/1999 | Sundstrom et al. | |
| 6,019,783 A | 2/2000 | Philips et al. | |
| 6,047,106 A | 4/2000 | Salyer | |
| 6,083,418 A | 7/2000 | Czarnecki et al. | |
| 6,117,164 A | 9/2000 | Gildersleeve et al. | |
| 6,197,045 B1 | 3/2001 | Carson | |
| 6,238,427 B1 | 5/2001 | Matta | |
| 6,257,011 B1 | 7/2001 | Siman-Tov et al. | |
| 6,319,599 B1 * | 11/2001 | Buckley | 428/308.4 |
| 6,349,560 B1 | 2/2002 | Maier-Laxhuber et al. | |
| 6,354,099 B1 * | 3/2002 | Bieberich | 62/259.3 |
| 6,364,937 B1 | 4/2002 | McMahon | |
| 6,375,674 B1 * | 4/2002 | Carson | 607/104 |
| 6,389,839 B1 | 5/2002 | Sabin | |
| 6,436,130 B1 | 8/2002 | Philips et al. | |
| 6,454,792 B1 | 9/2002 | Noda et al. | |
| 6,463,212 B1 | 10/2002 | Salyer | |
| 6,503,297 B1 | 1/2003 | Lu et al. | |
| 6,508,859 B1 | 1/2003 | Zia et al. | |
| 6,559,096 B1 | 5/2003 | Smith et al. | |
| 6,584,797 B1 | 7/2003 | Smith et al. | |
| 6,591,630 B2 | 7/2003 | Smith et al. | |
| 6,601,404 B1 | 8/2003 | Roderick | |
| 6,620,187 B2 | 9/2003 | Carson et al. | |
| 6,645,232 B2 | 11/2003 | Carson | |
| 6,669,715 B2 | 12/2003 | Hoglund et al. | |
| 6,688,132 B2 | 2/2004 | Smith et al. | |
| 6,692,518 B2 | 2/2004 | Carson | |
| 6,701,724 B2 | 3/2004 | Smith et al. | |
| 6,755,801 B2 | 6/2004 | Utterberg et al. | |
| 6,802,855 B2 | 10/2004 | Ellingboe et al. | |
| 6,818,012 B2 | 11/2004 | Ellingboe | |
| 6,858,068 B2 | 2/2005 | Smith et al. | |
| 6,878,156 B1 | 4/2005 | Noda | |
| 6,960,243 B1 | 11/2005 | Smith et al. | |
| 6,968,711 B2 | 11/2005 | Smith et al. | |
| 7,022,099 B2 | 4/2006 | Litzie et al. | |
| 7,063,718 B2 | 6/2006 | Dobak, III | |
| 7,097,657 B2 | 8/2006 | Noda et al. | |
| 7,172,586 B1 | 2/2007 | Dae et al. | |
| 7,827,815 B2 | 11/2010 | Carson et al. | |
| 8,047,010 B2 | 11/2011 | Carson et al. | |
| 2003/0150232 A1 | 8/2003 | Brudnicki | |
| 2006/0030916 A1 | 2/2006 | Lennox | |
| 2006/0074469 A1 | 4/2006 | Lennox et al. | |
| 2006/0124141 A1 | 6/2006 | Dobak, III | |
| 2006/0136023 A1 | 6/2006 | Dobak, III | |
| 2006/0161232 A1 | 7/2006 | Kasza et al. | |
| 2006/0247744 A1 | 11/2006 | Nest et al. | |
| 2006/0287697 A1 | 12/2006 | Lennox | |
| 2007/0043409 A1 | 2/2007 | Brian, III et al. | |
| 2008/0255644 A1 | 10/2008 | Carson | |
| 2009/0099629 A1 | 4/2009 | Carson et al. | |
| 2009/0131835 A1 | 5/2009 | Voorhees et al. | |

* cited by examiner

SORPTION-BASED ADHESIVE CONTACT COOLING APPARATUS AND METHOD

RELATED APPLICATIONS

This application claims priority to U.S. Patent Provisional Application Ser. No. 60/911,464, filed Apr. 12, 2007, entitled "SORPTION-BASED ADHESIVE CONTACT COOLING APPARATUS AND METHOD", the entirety of which is hereby incorporated by reference.

FIELD OF THE INVENTION

The present invention generally relates to a sorption-based, adhesive contact-cooling apparatus and method for cooling a patient. The invention is particularly apt for treating stroke, head trauma and cardiac arrest patients in an ambulatory vehicle or other emergency treatment site.

BACKGROUND OF THE INVENTION

The therapeutic use of rapid bodily cooling systems is ever-increasing. Of particular interest, it is now accepted that rapid cooling of stroke, cardiac arrest and head trauma patients can yield significant therapeutic benefits. Specifically, research indicates that even though a stroke or cardiac arrest victim's brain cells may loose their ability to function, the cells do not necessarily die quickly. In fact, brain damage from a stroke or cardiac arrest may take hours to reach maximum effect. Neurological damage may be reduced and the stroke or cardiac arrest victims' outcome improved if a neuroprotectant therapy is applied within this time frame.

Similarly, elements in the genesis of a traumatic brain injury (e.g., resulting from falls, vehicular accidents and the like) are now understood to overlap with elements in the genesis of neurological damage in stroke victims. In particular, delayed secondary injury at the cellular level after the initial head trauma is now recognized as a major contributing factor to the ultimate tissue loss that occurs after brain injury. Again, neurologic damage may be reduced if a neuroprotectant therapy is rapidly applied. Further, in this regard, studies have shown that treatment with mild hypothermia, defined as lowering core body temperature at 2-3 C.° confers neuroprotection in stroke victims, and may hasten the neurologic recovery and improve outcomes when applied for 12-72 hours in cases of traumatic head injury. Again, to optimize such therapies, the neuro-protective therapy should be initiated as soon as possible after a stroke or traumatic head injury.

As these and other medical applications for rapid bodily cooling have continued to evolve, the present inventors have recognized the desirability of enhancing the portability, stowability and ease-of-use of patient cooling systems so that patient treatment may be promptly initiated. More particularly, while known patient cooling systems have proven effective for many applications, the present inventors have recognized that additional emergency-oriented applications can be realized via the implementation of further improved liquid cooling methodologies and stand-alone componentry, as well as enhanced componentry packaging. In this regard, the present inventors have recognized the need for a cooling system and related methodology that is particularly apt for use in ambulatory settings, including, in particular, use in emergency vehicles such as helicopters, ambulances and the like where space utilization is at a premium and patient access may be limited.

SUMMARY OF THE INVENTION

In view of the foregoing, a primary objective of the present invention is to provide a portable patient cooling apparatus and related method that reduces space storage and emergency treatment site space requirements, is light weight and yields highly effective patient cooling.

A further objective of the present invention is to provide an apparatus and method for patient cooling that is easy to set-up and is otherwise user-friendly.

Another objective of the present invention is to provide an on-demand patient cooling apparatus and method that reduces or avoids the need for electrical or other emergency treatment site power utilities.

Another objective of the present invention is to provide an improved patient cooling apparatus and method that is cost effective.

Yet another objective of the present invention is to provide an apparatus and method for patient cooling that is adapted for single patient use and ready disposal.

These and other objectives and advantages are achieved by one or more aspects of the present invention. According to one aspect of the present invention, an inventive apparatus is provided that includes a pad for contacting and thereby absorbing heat from a patient. The pad comprises a fluid containing layer and an adhesive contact surface disposed on one side of the fluid containing layer for intimately contacting a patient to yield conductive cooling. The inventive apparatus further includes a sorption-based device, fluidly interconnectable to the fluid containing layer of the pad, for selectively vaporizing fluid contained in the fluid containing layer of the pad and for sorping the vaporized fluid to yield a cooling effect at the adhesive contact surface.

As will be appreciated, the combinative employment of a sorption-based device and adhesive contact cooling surface not only yields rapid, conductive patient cooling across the contact surface of the pad, but also facilitates the realization of numerous additional benefits, including enhanced portability, stowability and efficient, on-demand cooling. Further, the combinative employment of a sorption-based device and adhesive contact pad avoids the need for electrical or other power requirements for patient cooling.

The sorption-based device may be provided with an internal pressure that is less than an internal pressure of the fluid containing layer of the pad, e.g., prior to use. In one approach, an enclosed volume of the sorption-based device may be maintained at a predetermined subatmospheric pressure, e.g., a predetermined subatmospheric pressure less than about 5 hectopascals (hPa). By virtue of the internal pressure differential between the sorption-based device and fluid containing layer of the pad, vaporization of fluid within the fluid containing layer may be facilitated upon the establishment of a fluid interconnection between the fluid containing layer and sorption-based device.

The apparatus may include at least one port control member for selectively controlling at least one port that fluidly interconnects the fluid containing layer and sorption-based device. In one approach, a port control member may be manually moveable from a first position in which the port is closed to another position in which the port is open. In this regard, the port control member may be completely removable from or interconnected/moveable relative to the apparatus. Further, the port control member may be provided to allow for selective control over the size of a fluid interconnection opening defined by the port, wherein user control over a rate of cooling may be realized.

In one embodiment, the port may be biased to automatically open when the port control member is moved from the first position. By way of example, a port comprising a flexible material and an interconnected, interfacing spring member may be utilized, wherein the spring member is of a loop-type configuration and is biased to automatically expand from a closed-loop to an open-loop configuration when an external port control member is moved relative thereto, e.g., disengaged therefrom.

In one embodiment, the fluid containing layer of the apparatus may be of a pliable or flexible construction on at least said adhesive contact side thereof, thereby facilitating conformal and intimate contact interface with a patient. Further, the fluid containing layer may include an enclosure and a fluid retention member, located within the enclosure adjacent to the contact side of the pad, for retaining fluid. In the latter regard, the fluid retention member may include an open porous material, wherein the retention of fluid is distributed across a lateral extent of the fluid retention member. For example, it may be preferable for the fluid to be retained in a relatively uniform amount per unit volume across the lateral extent of the fluid retention member, thereby facilitating more uniform fluid vaporization and thermal exchange across the lateral extent of the pad of the inventive apparatus. In one embodiment, the fluid retention member may comprise a woven or non-woven material (e.g., a fabric material).

As noted, the apparatus may include at least one port disposed between the fluid containing layer of the pad and the sorption-based device. In turn, in one embodiment, the fluid containing layer may further include a first path defining means, located within an enclosure adjacent to a fluid retention member, for defining a first plurality of vaporized fluid diffusion paths between the fluid retention member and the at least one port. As may be appreciated, the first path defining means facilitates diffusion of vaporized fluid across the lateral extent of the fluid containing layer. In this regard, the first plurality of vaporized fluid diffusion paths may have corresponding end locations that are distributed across the lateral extent of the fluid retention member (e.g., spaced lengthwise and widthwise across the pad), thereby facilitating more uniform diffusion of vaporized fluid and corresponding thermal exchange.

In one embodiment, a first plurality of vaporized diffusion paths may include fluidly interconnected, tortuous paths. In this regard, the first plurality of vaporized fluid diffusion paths may each pass through at least two layers. For example, the first path defining means may be defined by a first plurality of elongated members arranged in the first layer and oriented in a first direction, and a second plurality of elongated members arranged in the second layer and orientated in a second direction transverse to said first direction (e.g., to define a cross-hatch pattern). The first plurality of elongated members may be arranged within the first layer in a parallel fashion and the second plurality of elongated members may be arranged in the second layer in a parallel fashion. In one implementation, the two layers of elongated members may be defined by a netting material.

In another embodiment, a first path defining means may be defined by plurality of projections, or dimples, that extend away from a backing surface (e.g., adjacent to a top side of the pad, opposite from the patient contacting side) in face-to face relation with a fluid retention member within the fluid containing layer. In turn, interconnected, tortuous pathways are defined around the projections and extend to at least one port for fluidly interconnecting the fluid containing layer and the sorption-based device.

In one approach, the apparatus may include a fluid containing layer that includes an enclosure that may be fluid-tight and restrict the passage of vapor and gas therethrough. For example, the enclosure may be of a multilaminate construction including a first vessel that comprises a fluid diffusion barrier material (e.g., a metal foil), and a second vessel comprising a reinforcement material (e.g., a polymer-based material). In one arrangement, two reinforcement layers are utilized, one comprising polyethylene and another comprising polyester.

The sorption-based device may include a sorption-based material for sorping vaporized fluid (e.g., a desiccant), and a second path defining means for defining a second plurality of vaporized fluid diffusion paths between the sorption material and at least one port that fluidly interconnects the sorption-based device fluid containing layer. As may be appreciated, the second path defining means may facilitate diffusion of vaporized fluid across the lateral extent of the sorption material. In this regard, the second plurality of vaporized fluid diffusion paths may have corresponding end locations that are distributed across the lateral extent of the sorption material, thereby facilitating uniform diffusion of vaporized fluid and corresponding sorption thereof.

The second plurality of vaporized diffusion paths may be provided to be tortuous paths. In one embodiment, the second plurality of vaporized fluid diffusion paths may each pass through at least two layers. For example, the first path defining means may comprise a first plurality of elongated members arranged in the first layer and oriented in a first direction, and a second plurality of elongated members arranged in the second layer and orientated in a second direction transverse to said first direction (e.g., to define a cross-hatch pattern). The first plurality of elongated members may be arranged within the first layer in a parallel fashion and the second plurality of elongated members may be arranged in the second layer in a parallel fashion. In one embodiment, the two layers of elongated members may be defined by a netting material.

Additionally, the sorption-based device may comprise at least one spacer member extending through the sorptive material to define at least one corresponding channel for receiving vaporized fluid therethrough, wherein the vaporized fluid may achieve increased contact with the sorption material. More preferably, a plurality of spacer members may be provided to define a corresponding plurality of channels that extend through the sorptive material in spaced relation to each other so as to further provide for enhanced contact between vaporized fluid and sorptive material. In turn, such increased contact yields increased/efficient liquid cooling capabilities, thereby facilitating rapid patient cooling. In one embodiment, a plurality of spacer members are oriented transverse to a second path defining means (e.g., perpendicular), wherein vaporized fluid is distributed across end locations of a plurality of channels for diffusion into and distribution along the plurality of channels.

The sorption-based device also may be provided to include a phase-change material (e.g., a hydrated salt or paraffin-based material) for extracting thermal energy attendant to sorption of vaporized fluid by the sorptive material. In this regard, it is preferable that at least a portion of the phase-change material be located directly adjacent to at least a portion of the sorptive material. By way of example, a plurality of spacer members may be disposed transversely to a second path defining means, with sorptive material located adjacent to each side of each spacer member and a phase-change material disposed therebetween (e.g., to yield a multilayered, laminar arrangement). In such an arrangement, a fluid diffusion barrier may be disposed between the adjacently located sorptive material and phase-change material. For example, the phase-change material may be disposed within a sealed pouch comprising a metal-based foil.

The adhesive contact surface of the apparatus may be provided to have a peel strength of approximately 10 gm/inch, thereby facilitating the establishment and maintenance of intimate contact for thermal exchange with a patient, while accommodating removal of the pad after use. In one approach, a removable liner may be provided across the adhesive surface and may be readily removable, e.g. for removal immediately prior to use of the apparatus.

In one embodiment, a conformable, thermally-conductive layer may be disposed between an adhesive contact surface and fluid containing layer of the pad. The conformable, thermally-conductive layer may be sufficiently thick and comprised of a sufficiently conformable material so as to conform to the contours of a patient's skin and envelop skin hair. As a result, insulating air pockets between the pad and the skin of a patient may be reduced. The conformable, thermally-conductive layer also provides for efficient thermal exchange therethrough between the skin of a patient and the fluid containing layer. In this regard, the conformable, thermally-conductive layer may advantageously comprise of a material having a coefficient of thermal conductivity of at least about 2 cal/hr-cm-° C.

The conformable, thermally-conductive layer may comprise a first material, such as a liquid (e.g., water), suspended in a matrix defined by a second material, such as a polymer. In this regard, the liquid preferably comprises between about 30 to 95 percent by weight of the total weight of the first and second materials.

The adhesive surface and thermally-conductive layer may be separately comprised of distinct materials. Alternatively, a thermally-conductive layer may be comprised of a hydrogel material having sufficient adhesive properties so as to integrally provide the adhesive surface.

In one implementation, an insulating layer may be disposed on the side of the pad not intended for patient contact (e.g., a top side). The insulating layer inhibits heat transfer between the surrounding air and the fluid containing layer, thereby enhancing the efficiency of the pad. Preferably, the insulating layer is comprised of a material having a coefficient of thermal conductivity of less than about 1.00 cal/hr-cm-° C.

As may be appreciated, the present invention further provides an inventive method for providing a cooled contact surface, e.g., for contact cooling a patient. The method comprises the steps of vaporizing fluid contained in a fluid containing layer of a contact pad having an adhesive surface for patient contact, and sorping the vaporized fluid within a sorption-based device, fluidly interconnectable to the fluid containing layer, wherein a cooled adhesive surface is provided on the contact pad.

The method may include the step of selectively establishing fluid interconnection between the fluid containing layer of the contact pad and the sorption-based device. By way of example, the selectively establishing step may provide for the control of a port, located between the fluid containing layer and the sorption-based device, from a closed position to an open position. In another approach, the establishing step may provide for controlling a degree of fluid interconnection so as to control a rate of cooling, e.g., by controlling the size of an opening defined by the port. In such approaches, a port control member may interface with and be moveable relative to the port to yield the desired control. In one arrangement, port control may be achieved by simply removing a port control member from the port. In one implementation, the port may be biased, e.g., spring loaded, wherein the port moves automatically opens upon relative movement, e.g., removal of a port control member relative to the port.

The method may further include the steps of providing a sorption-based device at an internal pressure less than an internal pressure of the fluid containing layer prior to fluid interconnection therebetween. In one approach, the sorption-based device may be provided at a predetermined subatmospheric pressure. In turn, upon the establishment of fluid interconnection between the sorption-based device and fluid containing layer, the differential pressure automatically facilitates vaporization of fluid within the fluid containing layer of the pad.

The vaporizing step of the method may provide for vaporization of fluid contained in a fluid retention member, located within the fluid containing layer, across the lateral extent of the fluid retention member. That is, by retaining fluid in a fluid retention member, a more uniform vaporization and cooling effect may be realized. In turn, the method may also include a step of diffusing vaporized fluid across the lateral extent of the fluid retention member to at least one port disposed between the fluid containing layer and the sorption-based device. In this regard, such diffusion may be achieved by passing the vaporized fluid through each of a plurality of vapor diffusion paths defined between the fluid retention member and the port(s).

The method may include the step of disposing a sorption material between each of a plurality of spacer members located within the sorption-based device. Correspondingly, the method may provide for diffusion of the vaporized fluid between at least one port, located between the fluid containing layer and the sorption-based device, and ends of the plurality spacer members. In this regard, diffusion of the vaporized fluid may be provided along a plurality of diffusion paths. By way of example, the plurality of diffusion paths may be defined by a path defining means, wherein the plurality of spacer members may be oriented in a transverse manner to the path defining member. In such an arrangement, the path defining means effectively functions to distribute vaporized fluid laterally along the diffusion paths to the ends of each of a plurality of channels defined by the spacer members.

The method may further provide for extracting thermal energy released in conjunction with the sorption of vaporized fluid. In this regard, a phase-change material may be utilized to extract the thermal energy. In one embodiment, a phase-change material may be disposed in adjacent to a sorption material between each pair of a plurality of spacer members within a sorption-based device.

The method may include the step of contacting the adhesive contact surface of the pad to a patient during at least a portion of the vaporizing step and said sorption step, wherein thermal energy is conductively transferred from the patient to said pad across the adhesive contact surface. Further, the contacting step may include the substep of removing a protective liner from the adhesive surface prior to the adhesively engaging step.

The method may further include the step of packaging the pad and sorption-based device together at a first location (e.g., a production facility), and unpackaging such components at a second location (e.g., an emergency patient care site) prior to use. Relatedly, the fluid containing layer of the pad and sorption-based device may be physically preconnected as packaged for ready fluid interconnection upon unpackaging, or may otherwise be adapted for ready physical connection after unpackaging.

Numerous additional aspects and advantages will become apparent to those skilled in the art upon consideration of further description that follows.

DETAILED DESCRIPTION OF THE INVENTION

Figure 1:
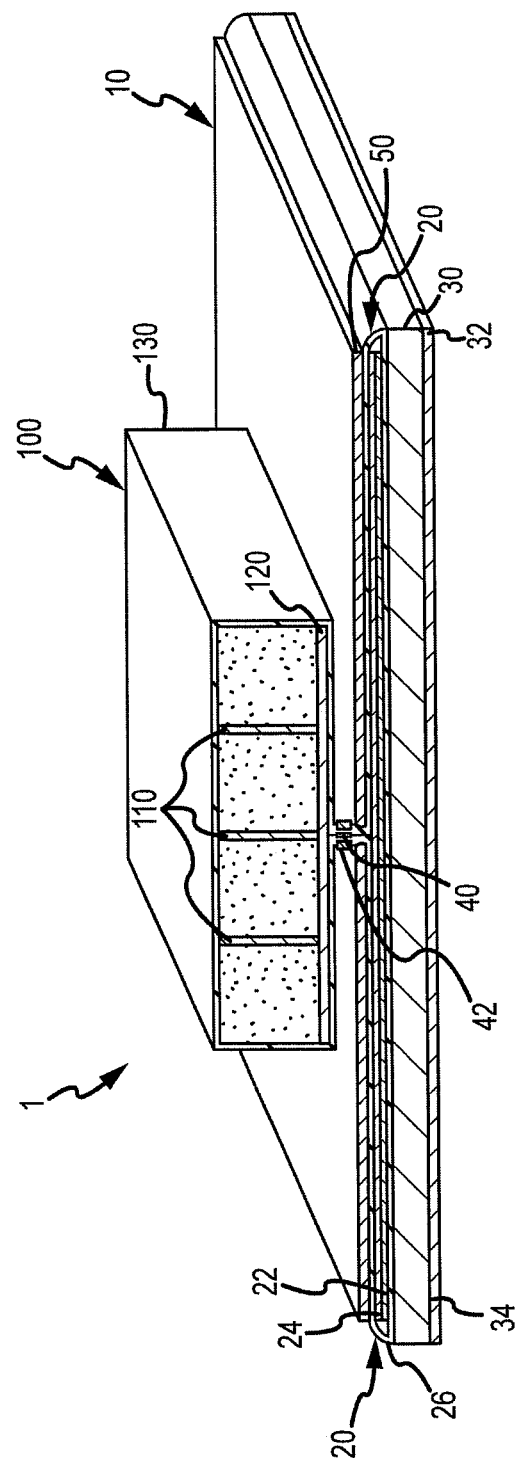
FIG. 1 is a cross-sectional, perspective view of one embodiment of the present invention shown prior to use.
Figure 2:
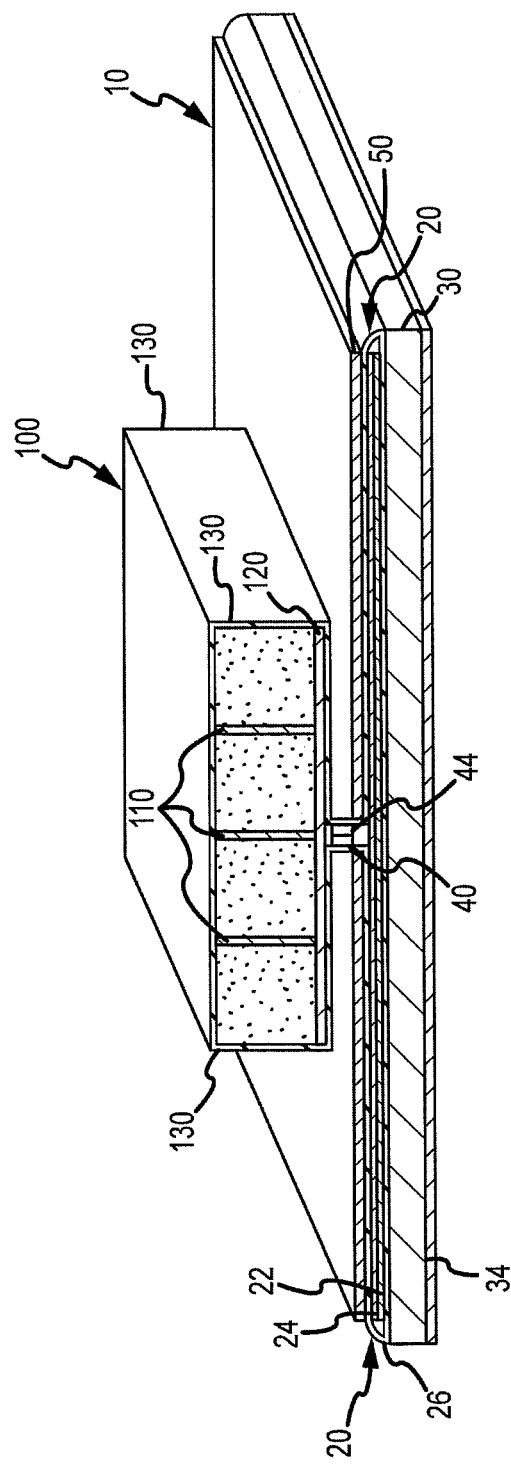
FIG. 2 is a cross-sectional, perspective view of the embodiment of FIG. 1, shown in an operative state.

FIGS. 1-4 illustrate one embodiment of the present invention. A cooling apparatus 1 includes a contact pad 10 for adhesively contacting a patient, and a sorption-based device 100 fluidly interconnectable with the contact pad 10. More particularly, the contact pad 10 includes a fluid containing layer 20 fluidly interconnectable to the sorption-based device 100 via a port 40. A port control member 42 may be disposed relative to port 40 so that when the port control member 42 is in the position shown in FIG. 1, port 40 is closed, and when the port control member 42 is removed from the port 40 as shown in FIG. 2, port 40 is open, as will be further described. In this regard, the sorption-based device may be provided to have an internal pressure less than that of the internal pressure of contact pad 10, prior to fluid interconnection therebetween. In one approach, the sorption-based device may have a subatmospheric pressure of less than about 5 hPa.

As shown, contact pad 10 may comprise a thermally-conductive layer 30 interconnected to fluid containing layer 20 on a bottom-side, or patient contact side thereof. In turn, a removable liner 32 may be connected to an adhesive contact side of the thermally-conductive layer 30, for selective removal prior to use. That is, upon removal of the liner 32, as shown in FIG. 2, an adhesive surface 34 may be exposed for contacting a patient. The thermally conductive layer 30 may comprise a hydrogel material that integrally defines the adhesive contact surface 32. For example, the conformable thermally conductive layer 30 and adhesive surface 32 may be comprised of an adhesive cross-linked hydrogel material such as "Polyhesive" manufactured by Valleylab of Boulder, Colo., is described in U.S. Pat. No. 5,645,855 to Lorenz. As further shown in FIGS. 1 and 2, the contact pad 10 may further include a thermally insulative layer 50 disposed on a top side of the fluid containing layer 20.

The fluid containing layer 20 may include a fluid retention member 22 and a flow path defining member 24 disposed in face-to-face, or laminate, fashion within a sealed enclosure 26. The fluid retention member 22 may comprise of material selected for retaining fluid in a distributed manner across the lateral extent (e.g., lengthwise and widthwise) of the fluid containing layer 20, wherein fluid retained by the fluid retention member 22 may vaporize across the lateral extent of contact pad 10 during use to facilitate efficient and uniform thermal exchange with a patient. Further in this regard, flow path defining member 24 may define a plurality of vaporized fluid diffusion paths between the fluid retention member 22 and port 40, thereby further facilitating efficient and uniform heat transfer during use.

In one approach, the fluid retention member 22 may comprise a woven or non-woven fabric. In the illustrated embodiment, the fluid containing layer 20 may include a vaporizable fluid as initially assembled and sealed. In other embodiments, it is contemplated that the vaporizable fluid may be selectively introduced into the fluid containing layer 20 via an openable/closeable port prior to use. In any case, the vaporizable fluid may comprise water in one approach. In one implementation, the flow path defining member 24 may comprise a netting material.

In one implementation, the sealed enclosure 26 may be fluid-tight and restrict the passage of vapor and gas therethrough. For example, the enclosure may be of a multilaminate construction including a first vessel that comprises a fluid diffusion barrier material (e.g., a metal foil), and a second vessel comprising a reinforcement material (e.g., a polymer-based material). In one arrangement, two reinforcement layers are utilized, one comprising polyethylene and another comprising polyester.

As shown in FIGS. 1 and 2, the sorption-based device 100 may comprise a plurality of spacer members 110 and a flow path defining member 120 disposed within an enclosure 130. The plurality of spacer members 110 each define a corresponding channel region therethrough for the passage of vaporized fluid. As shown, the spacer members 110 may extend transversely (e.g., (perpendicularly) away from flow path defining member 120. Between each of the adjacent spacer members 110 a sorptive material is provided, wherein vaporized fluid may contact and thereby be sorped by the sorptive material. Concomitantly, to extract thermal energy released in conjunction with such sorption, a phase-change material may be provided, e.g., adjacent to the sorptive material.

In one approach, the enclosure 130 may be fluid-tight and restrict the passage of vapor and gas therethrough. For example, the enclosure may be of a multilaminate construction including a first vessel that comprises a fluid diffusion barrier material (e.g., a metal foil), and a second vessel comprising a reinforcement material (e.g., a polymer-based material). In one arrangement, two reinforcement layers are utilized, one comprising polyethylene and another comprising polyester.

In one embodiment, the spacer members 110 may be defined by a netting material. More particularly, such netting may be an extruded material (e.g., comprising polyethylene or polypropylene) and may be of a woven nature so as to define corresponding channel regions. In turn, each spacer member 110 may define a corresponding channel region having a thickness, or width, of between about 0.5 mm and 2 mm for vaporized liquid refrigerant passage therethrough.

In one embodiment, the sorptive material may comprise a desiccant material. By way of example, the desiccant material may include one or more materials selected from a group consisting of: zeolite, barium oxide, activated alumina, silica gel, glycerine, magnesium perchlorate, calcium sulfate, calcium oxide, activated carbon, calcium chloride, glycerine silica gel, alumina gel, calcium hydride, phosphoric anhydride, phosphoric acid, potassium hydroxide and sodium sulfate.

An exemplary desiccant is a surface modified porous material. The porous material can be a material such as activated carbon or silica. The surface modification can include impregnating the porous material with one or more metal salts such as a metal salt selected from the group consisting of calcium chloride, lithium chloride, lithium bromide, magnesium chloride, calcium nitrate, potassium fluoride and the like. The porous support material is preferably loaded with from about 20 to about 80 weight percent of the metal salt and more preferably from about 40 to about 60 weight percent of the metal salt.

By way of example, the phase-change material may comprise a hydrated salt and/or a paraffin material. The phase-change material may have a transition temperature of from about 10° C. to about 80° C. More preferably, the phase-change material may have a transition temperature of at least about 25° C. It may be desirable to utilize phase-change materials that have a transition temperature above ambient (e.g., 25° C.) to simplify the storage of such materials. As used herein, transition temperature refers to the temperature at which the phase-change material undergoes a phase-change, e.g., from a solid to a liquid.

The phase-change material may also be provided to have a high energy density. The energy density may be measured in terms of mass (mass energy density) or volume (volumetric energy density). Mass energy density refers to the amount of energy that is released or adsorbed by the phase-change material per unit mass of the phase-change material. Volumetric energy density refers to the amount of energy that is released or adsorbed by phase-change material per unit volume of the phase-change material. Preferably, the phase-change material may have a volumetric energy density of at least about 200 $J/cm^3$, more preferably at least about 275 $J/cm^3$ and most preferably at least about 350 $J/cm^3$. Preferred phase-change materials include inorganic compounds such as disodium sulfate decahydrate, disodium hypophosphate dodecahydrate, barium hydroxide octahydrate, paraffins such as octadecane, and combinations thereof. In order to provide a range of transition temperature, it may be desirable to mix two or more phase-change materials.

In some embodiments, it may be desirable to restrict mixing of the desiccant and the phase-change material, especially at or above the transition temperature of the phase-change material. When the phase-change material is in a liquid or gas phase, as is the case above its transition temperature, it may cause unwanted chemical reactions with the desiccant or lessen thermal communication with the desiccant by reducing the amount of phase-change material in contact with the desiccant. In such a case, a fluid diffusion barrier may be employed to prevent the phase-change material from contacting the desiccant or from changing its shape. For example, the phase-change material may be disposed within a pouch that acts as a fluid diffusion barrier.

The fluid diffusion barrier can be any type of barrier which prevents the phase-change material from interspersing with the desiccant. Preferably, the fluid diffusion barrier also has a high thermal conductivity to enable efficient thermal communication between the desiccant and phase-change material. Preferred fluid diffusion barriers include simple plastic films such as polyethylene, nylon, PVC, metal foils with plastic heat seal layers such as those sold by Toyo Aluminum (Osaka, Japan), metallized plastic barriers such as those sold by DuPont (Wilmington, Del.) and Rexam (London, England), multilayer plastic layers and combinations thereof. In addition to preventing fluid diffusion, the phase-change material may be disposed within the fluid diffusion barrier to provide mechanical protection so that it retains its original shape and is resistant to physical or chemical changes in its structure. This may be accomplished by any means known in the art, including heat sealing.

Figure 3:
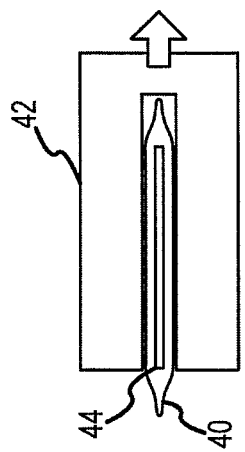
FIG. 3 is a cross-sectional, top view of a port and port control member of the embodiment shown in FIG. 1

Referring again now to FIG. 1, the port control member 42 may be disposed relative to port 40 so as to maintain the port 40 in a closed position prior to use. Further, liner 32 may be located on the thermally-conductive layer 30. To initiate use, the liner 32 may be removed from the thermally-conductive layer 30 and the port control member 42 may be removed from the port 40, as shown in FIG. 3. In the latter regard, the port 40 and port control member 42 may be provided so that on removal of the port control member 42, port 40 automatically opens.

Figure 4:
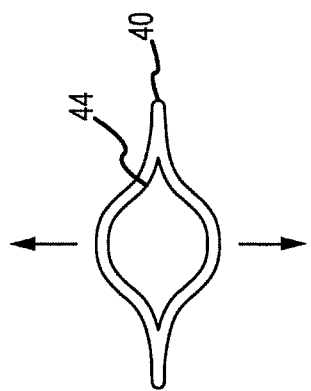
FIG. 4 is a cross-sectional, top view of a port and port control member of the embodiment shown in FIG. 2.

In this regard, reference is now made to FIGS. 3 and 4. As shown in FIG. 3, a u-shaped port control member is illustrated in contact engagement with port 42. In the latter regard, the port 40 may be provided with an internal spring member 44 that is biased so that the spring member 44 is in a collapsed state as shown in FIG. 3. In turn, upon removal of the port control member 42, as shown in FIG. 4, the spring member 44 automatically functions to mechanically open the port 40, wherein fluid interconnection between the fluid containing layer 20 and sorption-based device 100 is realized.

In this regard, it may be appreciated that the cooling apparatus 1 yields a convenient and easy to use solution for patient cooling. In particular, the cooling apparatus 1 may be packaged as a unit at a production location and shipped to an emergency patient care site for storage until needed. When needed for patient cooling, the cooling apparatus 1 may be removed from the packaging and positioned relative to a patient. In particular, the liner 32 may be readily removed from the adhesive contact surface 34. In turn, the adhesive contact surface may be positioned relative to and placed onto a patient, wherein an adhesive interface may be realized between the pad 10 of the cooling apparatus 1 and the patient. To initiate cooling, the port control member 42 may be simply removed from port 40, wherein the spring member 44 automatically opens the port 40 to establish a fluid interconnection between the contact pad 10 and sorption-based device 100. Pursuant thereto, the fluid in the fluid containing layer 20 of contact pad 10 may vaporize and concomitantly yield a cooling effect at the contact surface 34 so as to conductively absorb heat from the patient. In conjunction with fluid vaporization, the vaporized fluid may be sorped within the sorption-based device 100. In this regard, the cooling process may continue, free from the use of external power services, for an extended time, e.g., between about 15 minutes to several hours during which a patient may be transported by an emergency vehicle to a hospital or other primary patient care site.

The above-noted embodiments are for the purpose of illustration and are not intended to limit the scope of the present invention or patent. Rather, various modifications, adaptations and extensions of the invention will be apparent to those skilled in the art and are intended to be within the scope of the present invention.

What is claimed is:

1. An apparatus for contact cooling of a patient comprising:
 a pad having a fluid containing layer and an adhesive contact surface underlying one side of the fluid containing layer for adhesively contacting a patient; and,
 a sorption-based device, fluidly interconnectable to the fluid containing layer, for vaporizing fluid contained in the fluid containing layer and for sorping the vaporized fluid.

2. An apparatus as recited in claim 1, further comprising:
 a conformable layer disposed on said first side of the fluid containing layer, said conformable layer being thermally-conductive and defining said adhesive surface.

3. An apparatus as recited in claim 2, wherein said conformable layer comprises:
 a first material suspended in a matrix defined by a second material.

4. An apparatus as recited in claim 3, wherein said first material comprises a liquid and said second material comprises a polymer.

5. An apparatus as recited in claim 2, wherein said conformable layer comprises a hydrogel material.

6. An apparatus as recited in claim 1, wherein said fluid containing layer is pliable on at least one side thereof, and comprises:
 an enclosure; and,
 a fluid retention member, located within said enclosure adjacent to said one side for retaining said fluid.

7. An apparatus as recited in claim 6, wherein said fluid retention member comprises:

a porous material, wherein retention of said fluid is distributed across a lateral extent of said fluid retention member.

8. An apparatus as recited in claim 7, wherein said porous material is provided to retain a uniform amount of fluid per unit volume across said lateral extent.

9. An apparatus as recited in claim 7, wherein said porous material comprises a fabric material.

10. An apparatus as recited in claim 6, further comprising:
at least one port disposed between said fluid containing layer and said sorption-based device; and,
first path defining means, located within said enclosure adjacent to said fluid retention member, for defining a first plurality of vaporized fluid diffusion paths between said fluid retention member and said at least one port.

11. An apparatus as recited in claim 10, wherein first plurality of vaporized fluid diffusion paths are each of a tortuous configuration.

12. An apparatus as recited in claim 10, wherein said first plurality of vaporized fluid diffusion paths each pass through at least two layers.

13. An apparatus as recited in claim 10, wherein said first path defining means comprises:
a first plurality of elongated members arranged in said first layer and oriented in the first direction; and,
a second plurality of elongated members arranged in said second layer and oriented in the second direction transverse to the first direction.

14. An apparatus as recited in claim 10, wherein said first path defining means comprises:
a plurality of projections that extend away from a backing surface in face-to-face relation with said fluid retention member.

15. An apparatus as recited in claim 10, further comprising:
at least one port control member for selectively opening said at least one port to establish fluid interconnection between said fluid containing layer and said sorption-based device.

16. An apparatus as recited in claim 15, further comprising:
a conformable layer disposed on said first side of the fluid containing layer, said conformable layer being thermally-conductive and defining said adhesive surface.

17. An apparatus as recited in claim 16, wherein said conformable layer comprises:
a first material suspended in a matrix defined by a second material.

18. An apparatus as recited in claim 17, wherein said first material comprises a liquid and said second material comprises a polymer.

19. An apparatus as recited in claim 18, wherein said conformable layer comprises a hydrogel material.

20. An apparatus for contact cooling of a patient comprising:
a pad having a fluid containing layer and an adhesive contact surface underlying one side of the fluid containing layer for adhesively contacting a patient, said fluid layer being pliable on at least one side thereof and including an enclosure and a fluid retention member located within said enclosure adjacent to said one side for retaining said fluid;
a sorption-based device, fluidly interconnectable to the fluid containing layer, for vaporizing fluid contained in the fluid containing layer and for sorping the vaporized fluid;
at least one port disposed between said fluid containing layer and said sorption-based device; and
at least one port control member for selectively opening said at least one port to establish fluid interconnection between said fluid containing layer and said sorption-based device.

21. An apparatus as recited in claim 20, further comprising:
a conformable layer disposed on said first side of the fluid containing layer, said conformable layer being thermally-conductive and defining said adhesive surface.

22. An apparatus as recited in claim 21, wherein said conformable layer comprises:
a first material suspended in a matrix defined by a second material.

23. An apparatus as recited in claim 22, wherein said first material comprises a liquid and said second material comprises a polymer.

24. An apparatus as recited in claim 23, wherein said conformable layer comprises a hydrogel material.

* * * * *